(12) United States Patent
Kan et al.

(10) Patent No.: US 6,770,026 B2
(45) Date of Patent: Aug. 3, 2004

(54) OPERATING INSTRUMENT INSERTION APPARATUS AND OPERATION SUPPORTING APPARATUS

(75) Inventors: Kazutoshi Kan, Chiyoda (JP); Kouji Nishizawa, Tsuchiura (JP); Yasuhiro Nemoto, Ogawa (JP)

(73) Assignee: Hitachi, Ltd., Tokyo (JP)

( * ) Notice: Subject to any disclaimer, the term of this patent is extended or adjusted under 35 U.S.C. 154(b) by 70 days.

(21) Appl. No.: 10/180,030

(22) Filed: Jun. 27, 2002

(65) Prior Publication Data

US 2002/0169362 A1 Nov. 14, 2002

Related U.S. Application Data

(63) Continuation of application No. 09/520,850, filed on Mar. 8, 2000, now Pat. No. 6,497,651.

(30) Foreign Application Priority Data

Mar. 18, 1999 (JP) ............................................ 11-073162

(51) Int. Cl.$^7$ ................................................. A61B 1/04
(52) U.S. Cl. ........................ 600/114; 606/167; 606/185
(58) Field of Search ................................ 600/114, 104; 606/167, 184, 185, 190

(56) References Cited

U.S. PATENT DOCUMENTS

| | | | |
|---|---|---|---|
| 1,624,716 A | | 4/1927 | Cerbo |
| 2,621,651 A | | 12/1952 | Wallace |
| 4,721,116 A | | 1/1988 | Schintgen et al. |
| 4,836,205 A | | 6/1989 | Barrett |
| 5,320,627 A | * | 6/1994 | Sorensen et al. ........... 606/128 |
| 5,354,302 A | * | 10/1994 | Ko ............................. 606/104 |
| 5,445,142 A | | 8/1995 | Hassler, Jr. |
| 5,522,833 A | | 6/1996 | Stephens et al. |
| 5,893,863 A | | 4/1999 | Yoon |
| 6,099,550 A | | 8/2000 | Yoon |
| 6,139,508 A | | 10/2000 | Simpson et al. |
| 6,149,607 A | | 11/2000 | Simpson et al. |
| 6,159,207 A | | 12/2000 | Yoon |
| 6,190,399 B1 | | 2/2001 | Palmer et al. |
| 6,299,624 B1 | | 10/2001 | Cuschieri et al. |
| 6,447,444 B1 | * | 9/2002 | Avni et al. ................. 600/121 |

FOREIGN PATENT DOCUMENTS

| | | |
|---|---|---|
| DE | 196 05 615 A1 | 8/1997 |
| JP | 9-140659 | 6/1997 |
| WO | WO 83/03189 | 9/1983 |
| WO | WO 94/11052 | 5/1994 |

* cited by examiner

Primary Examiner—Beverly M. Flanagan
(74) Attorney, Agent, or Firm—Antonelli, Terry, Stout & Kraus, LLP

(57) ABSTRACT

There is provided an operating instrument insertion apparatus capable of easily inserting an operating instrument into the tissue. The operating instrument insertion apparatus includes a hollow tubular member for receiving an operating instrument therein, and a plurality of scoop-like members provided at a distal end of the hollow tubular member. The plurality of scoop-like members can be opened in such a manner that distal ends of the scoop-like members are moved away from each other in a direction transverse to an axial direction of said hollow tubular member, and the plurality of scoop-like members can be closed in such a manner that the distal ends of the scoop-like members are moved toward each other in this transverse direction, wherein the scoop-shape members in the opened condition cooperate so that an outside diameter formed thereby is no greater than an outside diameter of the hollow tube member.

12 Claims, 7 Drawing Sheets

OPERATING INSTRUMENT INSERTION APPARATUS AND OPERATION SUPPORTING APPARATUS

CROSS REFERENCE TO RELATED APPLICATION

This is a continuation of U.S. application Ser. No. 09/520,850, filed Mar. 8, 2000, now U.S. Pat. No. 6,497,651, the subject matter of which is incorporated by reference herein.

BACKGROUND OF THE INVENTION

This invention relates to an operating instrument insertion apparatus for inserting an operating instrument to the affected part while incising the tissue.

JP-A-9-140659 discloses an endoscope comprising an operation body portion, an insertion portion connected to the operation body portion for insertion into a body cavity, an illumination window provided at a distal end portion of the insertion portion, an observation window provided at the distal end portion of the insertion portion, a treatment instrument insertion channel provided in the distal end portion of the insertion portion, a nozzle provided at the distal end portion of the insertion portion for feeding air and water, and an operating knob mounted on the operation body portion for directing the distal end portion of the endoscope in a desired direction. The distal end surface of the distal end portion of the endoscope, at which the illumination window, the observation window, the treatment instrument insertion channel and the nozzle are provided, need to be flat, and therefore the distal end portion of the endoscope has a substantially cylindrical outer shape. In this endoscope, consideration is given to the insertion of the insertion portion through the oral cavity and the pharynx into the esophagus and further into the stomach and further into the duodenum, and in order to enable the insertion portion to be easily passed through narrow portions of the insertion path, a cap, having a streamline-shaped distal end, is fitted on the distal end of the endoscope. This cap can be removed from the insertion portion by projecting a forceps or the like from the distal end of the treatment instrument insertion channel.

The above conventional endoscope is designed to be inserted into a cavity in the human body having the insertion spaces (though narrow) such as the oral cavity, the pharynx, the esophagus, the stomach and the duodenum. Therefore, any consideration is not given to the insertion of the operating instrument into the tissue for the purpose of treating the affected part in the tissue.

SUMMARY OF THE INVENTION

It is an object of this invention to provide an operating instrument insertion apparatus capable of easily inserting an operating instrument into the tissue.

According to the present invention, there is provided an operating instrument insertion apparatus comprising a hollow tubular member for receiving an operating instrument therein, and a plurality of scoop-like members provided at a distal end of the hollow tubular member;

wherein the plurality of scoop-like members can be opened in such a manner that distal ends of the scoop-like members are moved away from each other in a direction transverse to a direction of insertion of the scoop-like members into the tissue, and the plurality of scoop-like members can be closed in such a manner that the distal ends of the scoop-like members are moved toward each other in the transverse direction.

In this construction, the plurality of scoop-like members, when opened, can spread the tissue, and by repeating this operation and the incision, the distal end of the tubular member can be inserted into a position near to the affected part. When the plurality of scoop-like members are opened, a treatment space, enabling the operation of the operating instrument, is formed between the distal end of the tubular member and the distal ends of the scoop-like members, and therefore the operating instrument can be projected into this space from the distal end of the tubular member so as to effect the treatment.

In the open condition of the plurality of scoop-like members, the operating instrument for incision purposes may be projected from the distal end of the tubular member so as to effect the incision. Alternatively, incision means such as a cautery knife may be provided at the distal end of the scoop-like member, and the incision can be effected in the closed condition of the plurality of scoop-like members.

DESCRIPTION OF THE PREFERRED EMBODIMENTS

A first embodiment of the present invention will now be described with reference to FIGS. 1 and 2.

Figure 1B:
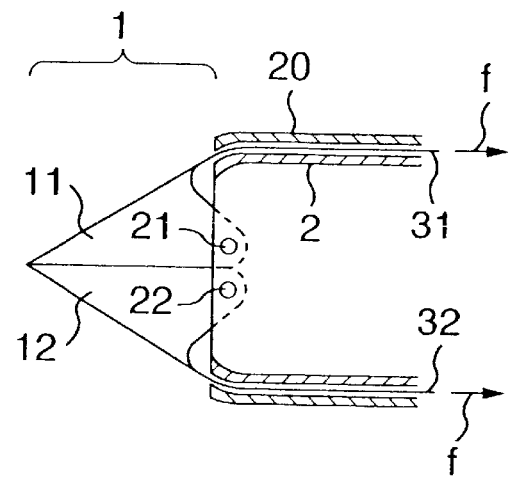
FIGS. 1A to 1C are views of a scoop-like member mechanism according to a first embodiment of an operating instrument insertion apparatus in accordance with the invention.
Figure 1A:
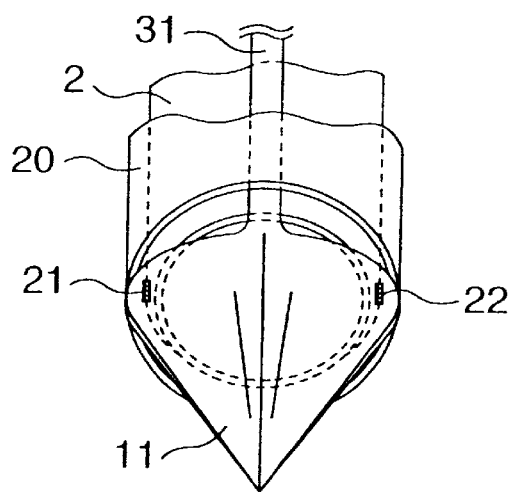
Figure 1C:
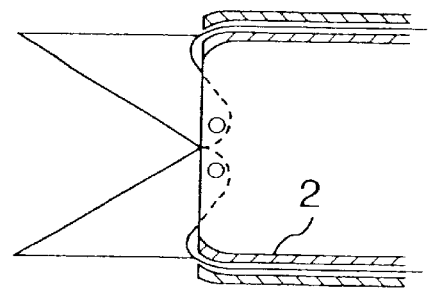

FIG. 1A is a perspective view of a distal end portion of an operating instrument insertion apparatus which can be inserted into the tissue, FIG. 1B is a cross-sectional view showing scoop-like or scoop-shape members in a closed condition, and FIG. 1C is a cross-sectional view showing the scoop-like members in an open condition.

As shown in FIGS. 1A to 1C, the apparatus of this embodiment includes the two scoop-like members 11 and 12, and the scoop-like member 11, as well as the scoop-like member 12, can be pivotally moved about pivot points 21 and 22 disposed on a common line or axis. The scoop-like members 11 and 12 are mounted on one end surface or a distal end surface of a hollow tubular member 2 or a peripheral surface of a distal end portion thereof. As shown in FIG. 1A, the two pivot points, disposed on the axis of pivotal movement, are provided at each scoop-like member. The cross-sectional shape of the hollow tubular member 2 is not limited to a circular shape, but can be an oval shape or a polygonal shape. In the case where the hollow tubular member 2 has a polygonal cross-sectional shape, it is preferred that corner portions be rounded.

Operating force-transmitting plate-like members 31 and 32 are connected respectively to the scoop-like members 11 and 12, and extend to the proximal end of the hollow tube 2, remote from the scoop-like members 11 and 12, over an outer peripheral surface thereof in the direction of the length thereof. An outer tube 20 covers the hollow tube 2, with the plate-like members 31 and 32 interposed between the hollow tube 2 and the outer tube 20. Thus, the plate-like members 31 and 32 are interposed between the hollow tube 2 and the outer tube 20, and have a plate-like shape, and therefore the plate-like members 31 and 32 will not be buckled and curved even when these plate-like members 31 and 32 are pulled and compressed upon application of an operating force. The plate-like members 31 and 32 have a sufficient rigidity to transmit this operating force. Further, the plate-like members 31 and 32 have such a flexibility that these members 31 and 32 are deformed along a curved surface of the distal end portion of the hollow tube 2 as shown in FIGS. 1B and 1C.

In this embodiment, although each of the operating force-transmitting members 31 and 32 comprises a plate-like member, this is not of absolute necessity, but can comprise a rigid wire such as a piano wire and a push rod, or any other suitable member. Each of the operating force-transmitting members 31 and 32 may comprise a thin sheet of metal, e.g. stainless steel, passing through a sheath-like guide tube. Each of the operating force-transmitting members 31 and 32 may be formed integrally with the associated scoop-like member, or may be a separate member connected to the associated scoop-like member.

When the plate-like members 31 and 32 are moved in a direction of arrow f (FIG. 1B), the scoop-like members 11 and 12 are pivotally moved about the pivot points as shown in FIG. 1C, so that the distal ends thereof are moved apart from each other in a direction transverse (or perpendicular) to a direction of insertion of the scoop-like members into the tissue, and are spaced a predetermined distance from each other. The scoop-like members 11 and 12 are formed such that the distance between their distal ends in this open condition is generally equal to the outer diameter of the hollow tube 2.

The two scoop-like members 11 and 12 in their closed condition (FIG. 1) are inserted into the tissue of the internal organ, and then the plate-like members 31 and 32 are driven to bring the scoop-like members 11 and 12 into the open condition shown in FIG. 1C, so that this tissue is forcibly spread or opened by the two scoop-like members 11 and 12. In this condition, an endoscope or an operating instrument, beforehand received in the hollow tube 2, is introduced into a space (formed between the distal end of the hollow tube 2 and the distal ends of the scoop-like members 11 and 12) formed in the tissue by the scoop-like members 11 and 12, so that the tissue of the internal organ can be observed or can be treated (see FIG. 5A).

In this condition, the incision and the hemostasis (if necessary) are effected. Then, the plate-like members 31 and 32 are moved in a direction opposite to the direction of arrow .t to bring the scoop-like members 11 and 12 into the closed condition shown in FIG. 1B, and then the scoop-like members 11 and 12 are inserted deeper into the tissue so that the distal end of the endoscope or the operating instrument, received in the hollow portion of the hollow tube 2, can be inserted into a predetermined position.

As described above, the two scoop-like members 11 and 12 have the function of spreading the relevant part of the tissue of the internal organ by moving their distal ends apart from each other to thereby form a space enabling the operation of the operating instrument. The two scoop-like members 11 and 12 also have the function of reducing the resistance which the hollow tube 2 receives during the inserting operation, and further have the function of enabling the hollow tube 2 to be less liable to be caught by the tissue.

In this embodiment, the two scoop-like members 11 and 12 may be replaced by four or more scoop-like members.

In this embodiment, preferably, the scoop-like members are made of a transparent material such as a plastics material so that they can be inserted into the tissue while obtaining information through an endoscope, and by doing so, the operability is enhanced.

Next, a drive mechanism (operating mechanism) for operating the scoop-like members will be described with reference to FIG. 2.

Figure 2:
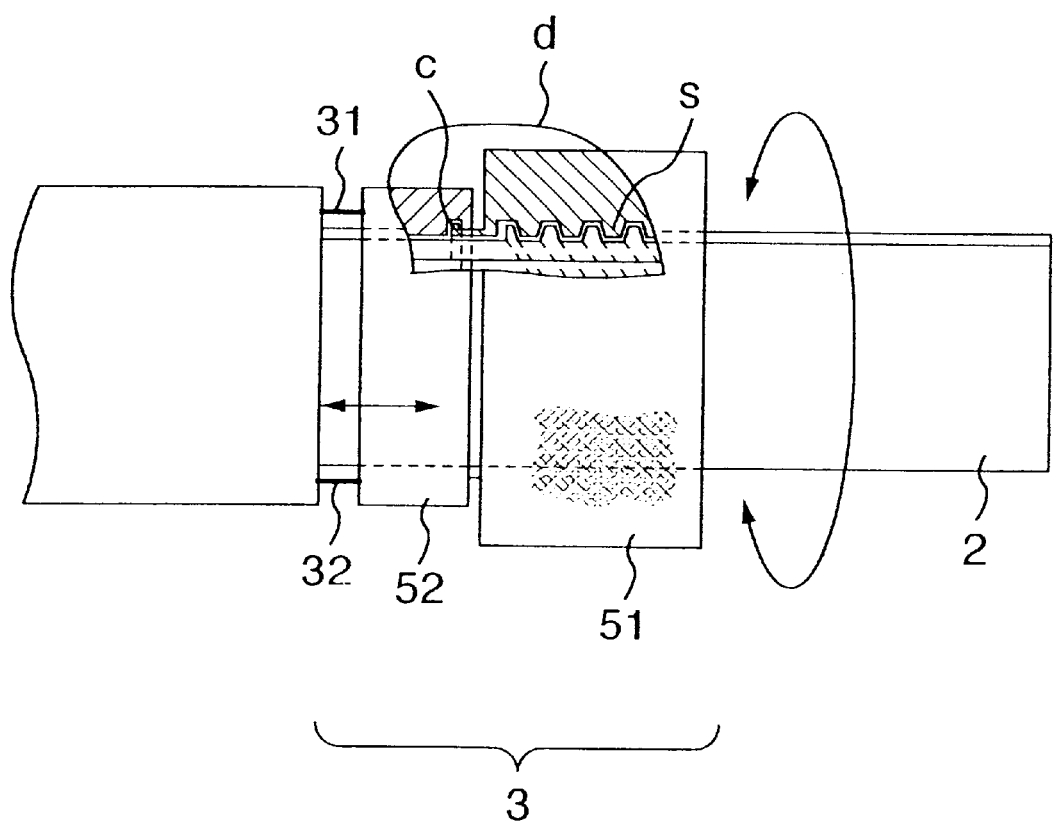
FIG. 2 is a cross-sectional, side elevational view of a drive mechanism of the apparatus of FIG. 1.

FIG. 2 is a partly-cross-sectional, side-elevational view of the drive mechanism portion.

The drive mechanism portion 3 for driving the scoop-like members 11 and 12 is provided at the proximal end portion of the hollow tube 2 (which comprises a flexibly-bendable tube as used in an endoscope) remote from the scoop-like members 11 and 12. The operating instrument can be inserted into the hollow portion (or the introducing tube) of the hollow tube 2 from the proximal end of this hollow tube 2 at which the drive mechanism portion 3 is provided.

The drive mechanism portion 3 includes a spiral thread, such as a screw thread, of a relatively large size, formed on the outer peripheral surface of the hollow tube 2 (as shown in a cross-section portion d of FIG. 2), and a manually-driving member 51 in mesh with this threaded portion. When the manually-driving member 51 is rotated about its axis by the operator, this manually-driving member 51 is moved along the hollow tube 2 through the threaded portion. A drive jig 52, to which the plate-like members 31 and 32 are connected, is connected to the manually-driving member 51 through a coupling c which can be freely rotated about its axis. Therefore, in accordance with the movement of the manually-driving member 51 along the hollow tube 2, the drive jig 52 is moved along the hollow tube 2, but is prevented from rotation about its axis. As a result, the plate-like members 31 and 32 are moved in the direction of the length of the hollow tube 2, so that the scoop-like members 11 and 12, provided respectively at the distal ends of the plate-like members 31 and 32, are pivotally moved in such a manner that the distal ends of the scoop-like members 11 and 12 are moved between their open and closed positions.

A modified drive mechanism portion (operating mechanism portion) 3 will be described with reference to FIG. 3.

Figure 3:
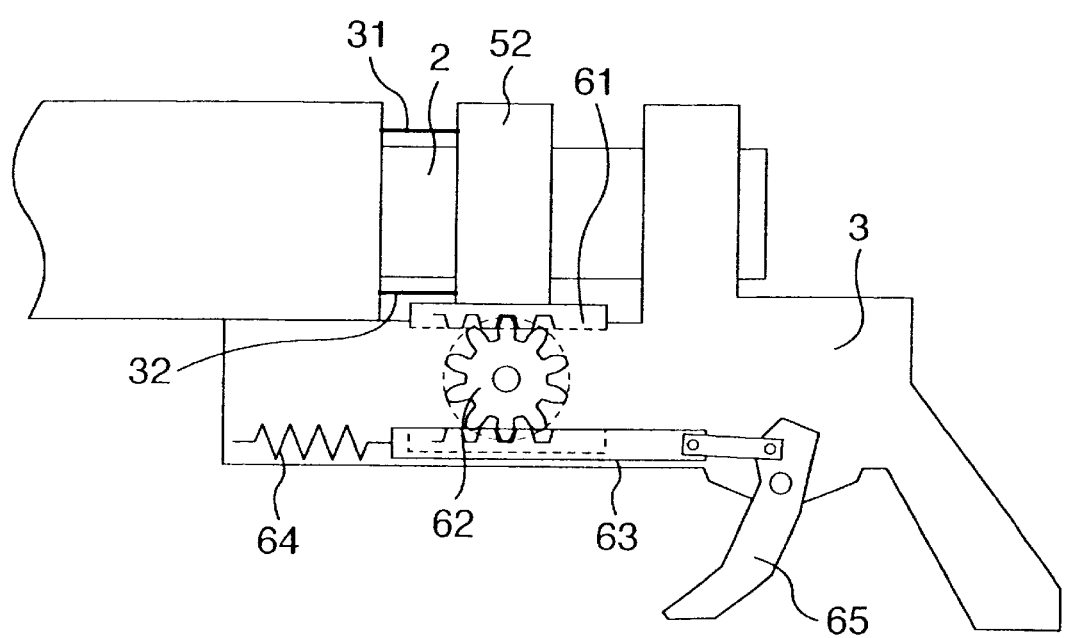
FIG. 3 is a side elevational view of a modified drive mechanism.

FIG. 3 is a side-elevational view of the drive mechanism portion 3.

In this embodiment, the operator holds the drive mechanism portion 3 with the hand, and manually inserts the insertion apparatus. A rack gear 61 is formed on a drive jig 52 to which the plate-like members 31 and 32 are connected, and the drive jig 52 is driven through a pinion gear 62 in mesh with the rack gear 61. This pinion gear 62 is in mesh with another rack gear 63, and the operator manually operates a knob 65 so as to drive the rack gear 63. Therefore, the drive jig 52 is moved along the hollow tube 2. When the operator reverses the knob 65, a spring 64 fixed the rack gear 63 automatically drive the rack gear 63 to an initial position. Therefore, the plate-like members 31 and 32 are moved in the direction of the length of the hollow tube 2, so that the scoop-like members 11 and 12, provided respectively at the distal ends of the plate-like members 31 and 32, are pivotally moved in such a manner that the distal ends of the scoop-like members 11 and 12 are moved between their open and closed positions.

Another modified drive mechanism portion (operating mechanism portion) 3 will be described with reference to FIG. 4.

Figure 4:
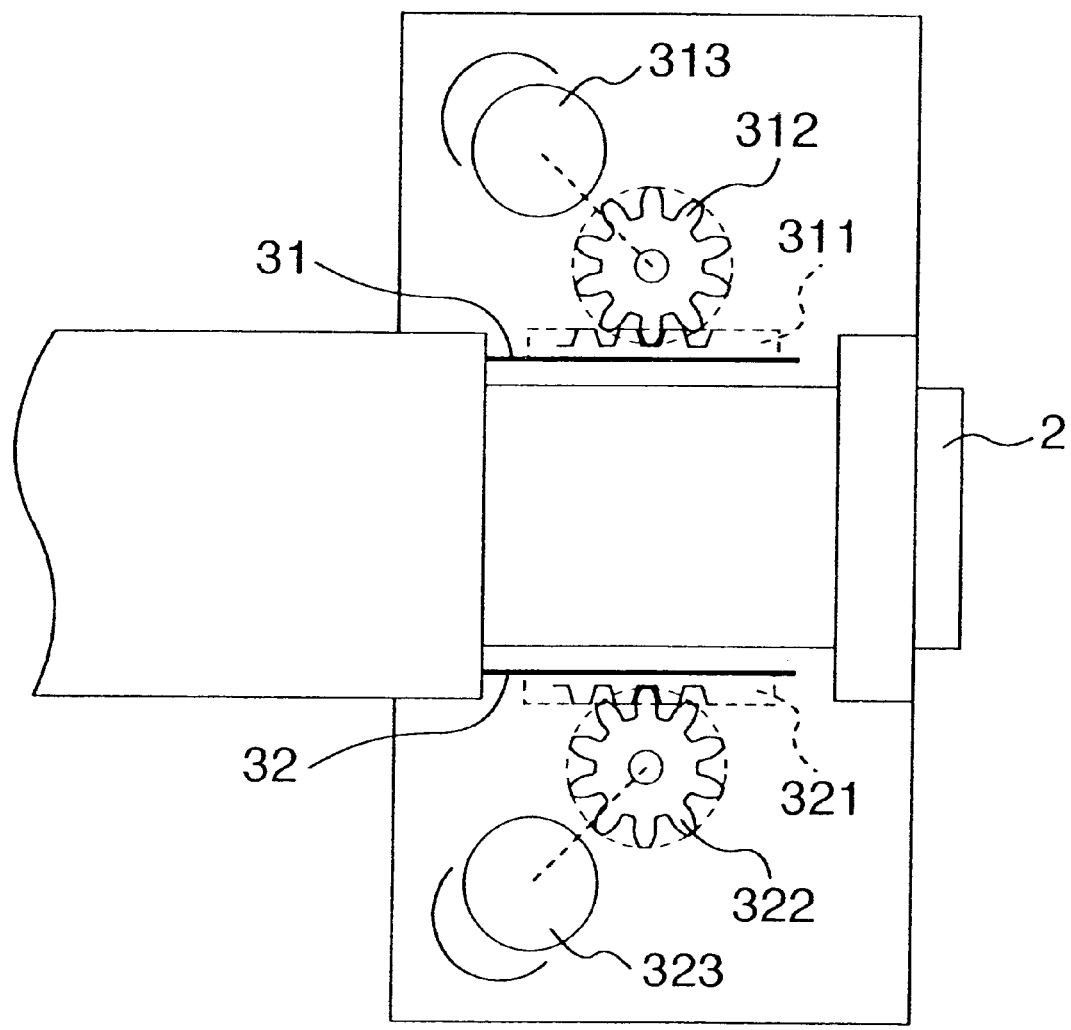
FIG. 4 is a side elevational view of another modified drive mechanism.

FIG. 4 is a side-elevational view of the drive mechanism portion.

The plate-like members 31 and 32 are connected to rack gears 311 and 321, respectively, and these rack gears 311 and 321 are in mesh with pinion gears 312 and 322, respectively. The pinion gears 312 and 322 are driven respectively by actuators which are pulse motors 313 and 323, respectively, in this example. When the operator operates an operation input switch (not shown in FIG. 4) for controlling the pulse motors 313 and 323, the plate-like members 31 and 32 are driven, and as a result the scoop-like members 11 and 12, provided respectively at the distal ends of the plate-like members 31 and 32, are pivotally moved in such a manner that the distal ends of the scoop-like members 11 and 12 are moved between their open and closed positions. Thus, the operator can control the operation of the scoop-like members 11 and 12 only by operating the switch, and therefore the operability is greatly enhanced.

Figure 5A:
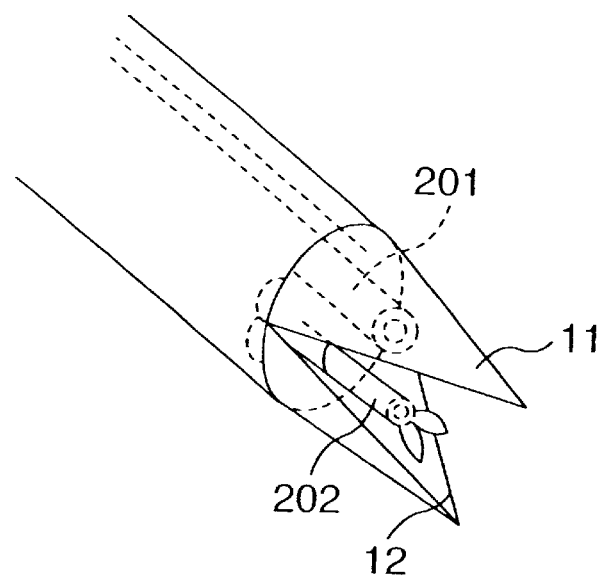
FIGS. 5A to 5C are perspective views of a scope-like member having an incision function according to another embodiment of the invention.

The manner of using the insertion apparatus of the above embodiment (FIGS. 1 to 4) will be described with reference to FIGS. 5A to 5C.

When the scoop-like members are to be inserted into the tissue of the non-tubular internal organ, the scoop-like members are combined together to jointly form a cone-shaped portion having a pointed distal end, and this cone-shaped portion is slightly inserted into the tissue of the internal organ while incising (or cutting) the surface of this tissue only at an initial stage of this inserting operation.

When the cone-shaped portion is this slightly inserted into the tissue, the plurality of scoop-like members are opened (or spread out) in such a manner that the distal ends thereof are moved apart from each other, thereby forcibly spreading the tissue of the internal organ. The open end of the hollow tube (tubular member) 2 is disposed at the proximal ends of the scoop-like members 11 and 12 as shown in FIG. 5A, and an endoscope 201 or an operating instrument 202 is projected outwardly from the hollow tube 2 through this open end, and therefore the tissue of the internal organ can be observed, or a suitable treatment can be effected for the affected part of this tissue. Namely, by providing the endoscope or the operating instrument in the hollow tube (tubular member) 2, an operation supporting apparatus can be provided.

For further inserting the scoop-like members into the tissue of the internal organ, this tissue is incised by a cautery knife or the like to thereby provide an insertion port, and a treatment such as hemostasis is performed, and then the plurality of scoop-like members are again moved into the closed condition, and the cone-shaped portion is inserted into the tissue.

Thus, the apparatus of the invention has the mechanism for driving the plurality of scoop-like members so as to secure a space, and also has the hollow portion through which an operating instrument, for example, for incision purposes can be passed. Therefore, the scoop-like members are spread out (or opened) to secure a space, and in this condition the tissue is incised, and then the scoop-like members are again closed into the cone-shape, and can be inserted into the tissue.

The scoop-like members in the closed condition is slightly inserted into the tissue, and are opened to forcibly spread this tissue to form a space. Then, the tissue is observed by an endoscope received in the hollow tube, and the incision and hemostasis are effected by the operating instrument received in the hollow tube. Then, the scoop-like members are again closed, and are inserted deeper into the tissue. By repeating this operation, the scoop-like members can be inserted into the tissue of the internal organ, such as the brain and the liver, while effecting the necessary treatments.

As shown in FIG. 53, an incision function such as a cautery knife can be provided at the distal end of the scoop-like member, and by doing so, the operability can be further enhanced. In this case, when the scoop-like members are spread out (or opened), the organ tissue can be directly incised while effecting the hemostasis. At this time, the treatment can be effected while observing the tissue through an endoscope or the like provided in the hollow tube 2.

Figure 5B:
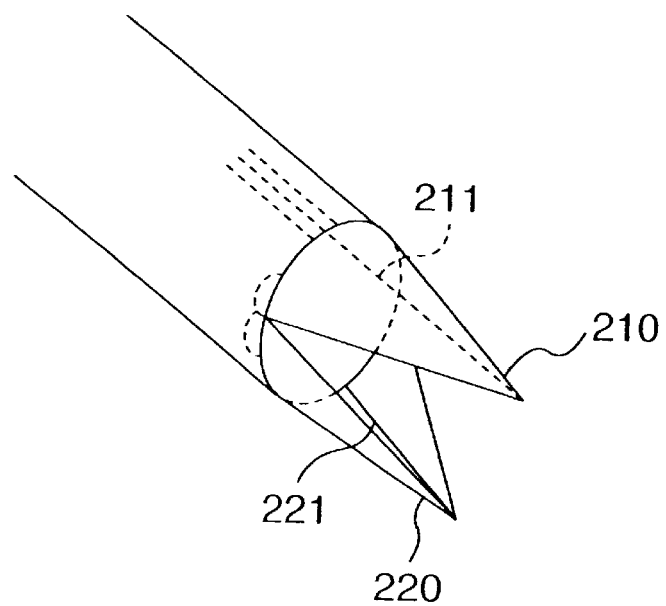
Figure 5C:
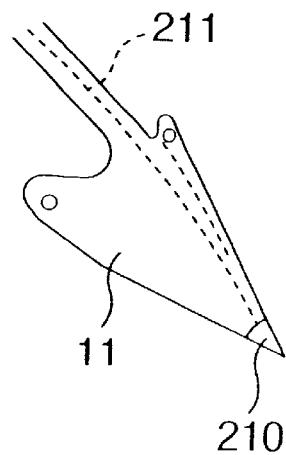

In this case, as shown in FIGS. 5B and 5C, the scoop-like member is made of a resin, and an electrode 210, 220 of the metal cautery knife is provided at the distal end thereof, and extends like a wire 211, 221.

An embodiment of an overall system, utilizing the apparatus shown in FIGS. 1A to 5C, will be described with reference to FIG. 6.

Figure 6:
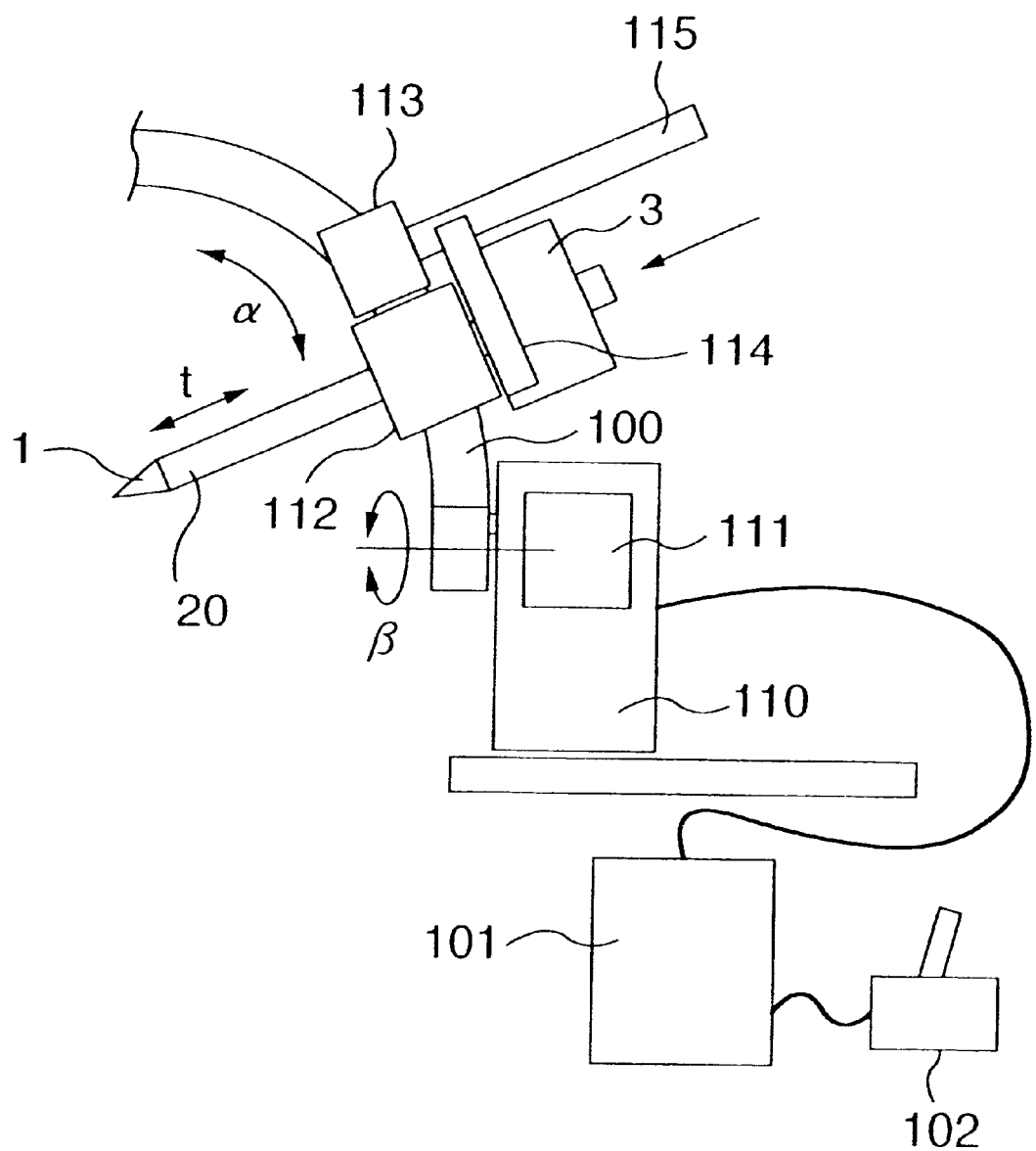
FIG. 6 is a side elevational view of an overall construction of an operation supporting apparatus according to the invention.

FIG. 6 is a side-elevational view showing the system construction of the operation supporting apparatus.

In this embodiment, the insertion apparatus, comprising scoop-like members 1, the hollow tube 2 and the drive mechanism portion 3, is held by a holding device 100, and the insertion apparatus is inserted into the tissue of the internal organ. In this embodiment, the insertion apparatus can be positioned in X-, Y- and Z-directions by an X-, Y- and Z-axis drive portion 110, and the rotation 13 of the insertion apparatus can be effected by a rotation (/3) drive portion 111, and the rotation a can be effected by a rotation (a) drive portion 112, and the translation t can be effected by a translation (t) drive portion 113. These drive portions can be operated by operation input means 102 through a control unit 101, and therefore the distal end of the hollow tube 2 can be easily located at the affected part. With respect to the translation (t) drive portion 113, a ball thread portion 115 is driven, so that a moving portion 114 in mesh with the ball thread portion 115 is moved, thereby effecting the translational movement.

With this construction, the operator does not need to hold the insertion apparatus with the hand, and therefore the operability is greatly enhanced. For moving the insertion apparatus in a direction of arrow j, the operator operates an operating lever 102 in accordance with this inserting direction so as to drive a drive device for controlling the upward and downward movement.

FIGS. 7A to 7D show various shapes of scoop-like members which can be used in the above embodiments.

Figure 7A:
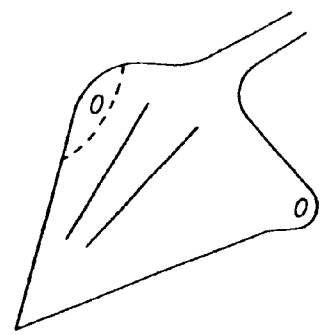
FIGS. 7A to 7D are perspective views of scoop-like members having various shapes applicable to the above embodiments of the invention.
Figure 7B:
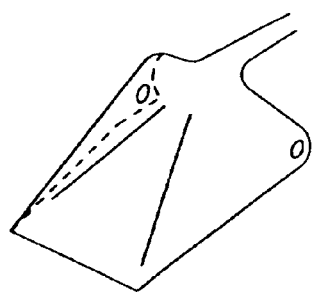
Figure 7C:
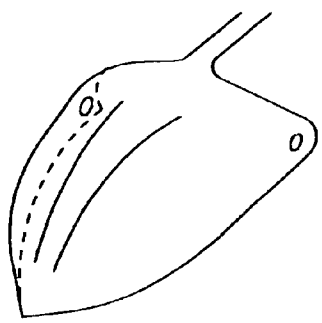
Figure 7D:
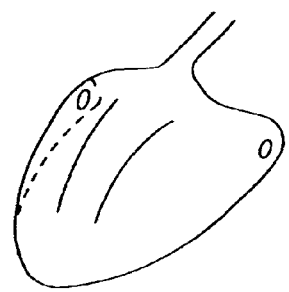

The scoop-like member, shown in FIG. 7A, is linearly tapering toward its pointed distal end, and the resistance to the insertion of this scoop-like member is small. The scoop-like member, shown in FIG. 73, is generally spatulate, and has a distal end portion of a relatively-large width, and when these scoop-like members are spread out (or opened), a space of a relatively large size can be secured. The scoop-like member, shown in FIG. 7C, is tapering toward its pointed distal end, with its distal end portion bulged or curved, and a relatively large space is defined by the inner surface of this scoop-like member. The scoop-like member, shown in FIG. 7D has a rounded distal end, and can be inserted into a relatively-soft tissue.

In the present invention, the plurality of scoop-like members are provided at the distal end of the hollow tubular member into which the operating instrument can be inserted. The plurality of scoop-like members can be opened in such a manner that the distal ends of the scoop-like members are moved away from each other in the direction transverse to the direction of insertion of the scoop-like members into the tissue, and the plurality of scoop-like members can be closed in such a manner that the distal ends of the scoop-like members are moved toward each other in this transverse direction. Thus, the scoop-like members can be repeatedly moved between their closed and open positions. Therefore, the relevant part of the tissue can be spread by opening the plurality of scoop-like members, and by repeating this operation and the incision of the tissue, the distal end of the tubular member can be inserted into a position near to the affected part.

What is claimed is:

1. An operating instrument insertion apparatus comprising a hollow tubular member for receiving an operating instrument therein, and a plurality of scoop-shape members provided at a distal end of said hollow tubular member;

wherein said plurality of scoop-shape members have a distal end, said plurality of scoop-shape members can be opened in such a manner that the distal ends of said scoop-shape members are moved away from each other in a direction transverse to an axial direction of said hollow tubular member, and said plurality of scoop-shape members can be closed in such a manner that the distal ends of said scoop-shape members are moved toward each other in said transverse direction;

wherein said scoop-shape members in the opened condition cooperate so that an outside diameter formed thereby is no greater than an outside diameter of said hollow tube member.

2. An operating instrument insertion apparatus comprising a hollow tubular member for receiving an operating instrument therein, and a plurality of scoop-shape members provided at a distal end of said hollow tubular member;

wherein said plurality of scoop-shape members have a distal end, said plurality of scoop-shape members are pivotally connected to the distal end of said tubular member so as to be pivotally moved radially of said tubular member;

there is provided an operating mechanism portion which can open said plurality of scoop-shape members in such a manner that the distal ends of said scoop-shape members are moved away from each other in a direction transverse to an axial direction of said hollow tubular member, and said operating mechanism can close said plurality of scoop-shape members in such a manner that the distal ends of said scoop-shape members are moved toward each other in said transverse direction;

wherein said scoop-shape members in the opened condition cooperate so that an outside diameter formed thereby is no greater than an outside diameter of said hollow tube member.

3. An operating instrument insertion apparatus comprising a hollow tubular member for receiving an operating instrument therein, a plurality of scoop-shape members provided at a distal end of said hollow tubular member;

wherein said plurality of scoop-shape members have a distal end said plurality of scoop-shape members are pivotally connected to the distal end of said tubular member; and wherein a plurality of operating members are connected respectively to said scoop-shape members so as to pivotally move said scoop-shape members, and extend to the other end of said tubular member along said tubular member;

wherein said scoop-shape members in the opened condition cooperate so that an outside diameter formed thereby is no greater than an outside diameter of said hollow tube member.

4. An operating instrument insertion apparatus comprising a hollow tubular member for receiving an operating instrument therein, and a plurality of scoop-shape members provided at a distal end of said hollow tubular member;

wherein said plurality of scoop-shape members have a distal end, said plurality of scoop-shape members can be opened in such a manner that the distal ends of said scoop-shape members are moved away from each other in a direction transverse to an axial direction of said hollow tubular member, and said plurality of scoop-shape members can be closed in such a manner that the distal ends of said scoop-shape members are moved toward each other in said transverse direction;

wherein when said scoop-shape members are opened, a space, into which said operating instrument can be projected from the distal end of said tubular member, is formed between the distal ends of said scoop-shape members and the distal end of said tubular member; and wherein said scoop-shape members in the opened condition cooperate so that an outside diameter formed thereby is no greater than an outside diameter of said hollow tube member.

5. An operating instrument insertion apparatus comprising a hollow tube, and a plurality of scoop-shape members pivotally connected to a distal end of said tube;

wherein said plurality of scoop-shape members, when closed to be combined together, jointly form a generally cone-shaped portion, tapering toward a distal end thereof, and covers a surface of the distal end of said tube, and when said plurality of scoop-shape members are spread away from an axis of said cone-shaped portion, the distal ends of said scoop-shape members are moved away from each other, and are disposed on a circle no larger than an outer diameter of said tube;

wherein an operating force-transmitting member is connected at a distal end thereof to each of said scoop-shape members, and extends so as to have a length along said tube, and a proximal end of said operating force-transmitting member is connected to a drive mechanism provided near a proximal end of said tube.

6. An operating instrument insertion apparatus according to any one of claims 1 to 5, in which each of said scoop-shape members is made of a transparent material.

7. An operating instrument insertion apparatus according to claim 5, in which said drive mechanism can drive said operating force-transmitting member in a direction of the length thereof.

8. An operation supporting apparatus comprising a hollow tubular member for receiving an operating instrument therein, and a plurality of scoop-like members provided at a distal end of said hollow tubular member;

wherein said plurality of scoop-like members can be opened in such a manner that distal ends of said scoop-like members are moved away from each other in a direction transverse to an axial direction of said hollow tubular member, and said plurality of scoop-like members can be closed in such a manner that the distal ends of said scoop-like members are moved toward each other in said transverse direction;

wherein the operating instrument is inserted in said tubular member; and wherein said scoop-shape members in the opened condition cooperate so that an outside diameter formed thereby is no greater than an outside diameter of said hollow tube member.

9. An operating instrument insertion apparatus according to any one of claims 1 to 4 and 8, wherein said plurality of scoop-like members which are provided at a distal end of said hollow tubular member are members which are separate from said hollow tubular member.

10. An operating instrument insertion apparatus according to claim 9, further comprising an outer tube covering at least a major portion of an axial length of said hollow tubular member, wherein said scoop-shape members in the open condition cooperate so that the outside diameter formed thereby is no greater than an inside diameter of said outer tube which covers said hollow tubular member.

11. An operating instrument insertion apparatus according to claim 5, wherein said plurality of scoop-like members which are provided at a distal end of said hollow tube are members which are separate from said hollow tube.

12. An operating instrument insertion apparatus according to claim 11, further comprising an outer tube covering at least a major portion of an axial length of said hollow tube, wherein said scoop-shape members in the open condition cooperate so that the outside diameter formed thereby is no greater than an inside diameter of said outer tube which covers said hollow tube.

* * * * *